(12) United States Patent
Paulsen

(10) Patent No.: US 7,540,036 B1
(45) Date of Patent: Jun. 2, 2009

(54) MEDICAL BIB

(76) Inventor: Julianne Paulsen, 9106 Heatherdale St., Santee, CA (US) 92071

( * ) Notice: Subject to any disclaimer, the term of this patent is extended or adjusted under 35 U.S.C. 154(b) by 0 days.

(21) Appl. No.: 11/960,633

(22) Filed: Dec. 19, 2007

(51) Int. Cl.
*A41D 13/04* (2006.01)
*A41D 13/12* (2006.01)

(52) U.S. Cl. .................. 2/49.1; 2/48; 2/171; 2/174

(58) Field of Classification Search ............. 2/49.1, 2/49.3, 49.4, 50, 174, 84, 88, 51, 114, 48, 2/171, 172, 173, 202, 204, 207, 209.13, 49.2, 2/52, 69.5, 89; 128/854, 849, 857, 872, 873, 128/874

See application file for complete search history.

(56) References Cited

U.S. PATENT DOCUMENTS

| | | | | | |
|---|---|---|---|---|---|
| 969,491 | A | * | 9/1910 | Payne | 2/174 |
| 1,511,737 | A | * | 10/1924 | Lord | 2/50 |
| 2,413,456 | A | * | 12/1946 | Larkin | 2/48 |
| 2,482,182 | A | * | 9/1949 | Henninger | 2/48 |
| 2,629,870 | A | * | 2/1953 | Hudson | 2/49.1 |
| 2,682,672 | A | * | 7/1954 | Moore | 128/872 |
| RE24,043 | E | * | 7/1955 | Barager | 2/49.2 |
| 3,781,916 | A | * | 1/1974 | Vitol | 2/88 |
| 4,370,755 | A | * | 2/1983 | Crumby | 2/88 |
| 4,445,231 | A | * | 5/1984 | Noel | 2/49.3 |
| 4,457,026 | A | * | 7/1984 | Morris | 2/171 |
| 4,601,065 | A | * | 7/1986 | Sigl et al. | 2/49.2 |
| 4,649,572 | A | * | 3/1987 | Roessler | 2/49.2 |
| 4,694,510 | A | * | 9/1987 | Kamrath | 2/49.1 |
| 5,042,507 | A | * | 8/1991 | Dowdy | 128/849 |
| 5,168,579 | A | * | 12/1992 | Marshall | 2/88 |
| 5,709,000 | A | * | 1/1998 | Hansen et al. | 5/655 |
| 5,855,021 | A | * | 1/1999 | Somerville | 2/84 |
| 6,269,815 | B1 | * | 8/2001 | Jascomb | 128/849 |
| 6,532,596 | B1 | * | 3/2003 | Fosmo | 2/49.1 |
| 7,181,771 | B1 | * | 2/2007 | Naehu | 2/49.1 |
| 2001/0047532 | A1 | * | 12/2001 | Marrero | 2/49.1 |

\* cited by examiner

*Primary Examiner*—Amy B Vanatta
(74) *Attorney, Agent, or Firm*—Eric Hanscom; Todd Langford

(57) ABSTRACT

A disposable medical bib that attaches around the neck of the patient on one side is disclosed. It not only protects the patient's chest from unwanted substances, but also includes a headrest cover and, optionally, the headrest itself. The medical bib can also optionally include a hairnet to contain the patient's hair. An alternative embodiment of the invention includes a pocket on the chest portion of the bib to collect unwanted substances, as well as a pocket on the headrest cover portion to hold items such as a headrest. A portion of the bib can be elongated to cover the midsection of the patient.

11 Claims, 6 Drawing Sheets

MEDICAL BIB

CROSS REFERENCE TO RELATED APPLICATIONS

None.

STATEMENT REGARDING FEDERALLY SPONSORED RESEARCH OR DEVELOPMENT

This invention was not federally sponsored.

BACKGROUND OF THE INVENTION

Field of the invention

This invention relates to the general field of medical bibs, and more specifically toward a disposable medical bib that attaches around the neck of the patient on one side. It not only protects the patient's chest from unwanted substances, but also includes a headrest cover and, optionally, the headrest itself. The medical bib can also optionally include a hairnet to contain the patient's hair. An alternative embodiment of the invention includes a pocket on the chest portion of the bib to collect unwanted substances, as well as a pocket on the headrest cover portion to hold items such as a headrest. A portion of the bib can be elongated to cover the midsection of the patient.

Bibs have been used in the medical and dental profession for a long period of time. They are used to protect the patient, or user, from unwanted substances and materials contacting his or her clothes or skin located beneath his or her face. Alligator clamps are commonly used to attach the bib around the patient's neck. These clips, however, must be sterilized after each and every use to prevent spread of disease. Sometimes the alligator clips are not sterilized, or not sterilized properly, and can needlessly spread disease from one patient to the next.

Medical and dental offices often have beds or chairs with headrests for the patient. Sometimes the headrests have coverings that must be replaced after each use by a patient. Alternatively, if there is no covering, the headrest must be cleaned after each use by a patient. Because of the large volume of patients that medical and dental professionals see each day, it can be commonplace to forget to replace the covering or clean the headrest. Failing to replace the covering or clean the headrest can lead to the spread of disease between patients.

Hairnets are also used during medical and dental procedures to restrict the movement of the patient's hair. These hairnets are generally disposable and separate from any other device. They can become dislodged or removed from the patient's head as the patient moves his or her head against a headrest.

Thus there has existed a long-felt need for a medical or dental bib that can be economically disposed of after every use. Further, there is a need for a medical or dental bib that can act as both a bib and a headrest with an optional hairnet that will reduce the likelihood that diseases will spread between patients. It should be easy to use and economical to manufacture so that each patient can easily use the medical bib and remove and dispose of it after each use.

The current invention provides just such a solution by having a disposable medical bib that attaches around the neck of the patient on one side. It not only protects the patient's chest from unwanted substances, but also includes a headrest cover and, optionally, the headrest itself. The medical bib can also optionally include a hairnet to contain the patient's hair. An alternative embodiment of the invention includes a pocket on the chest portion of the bib to collect unwanted substances, as well as a pocket on the headrest cover portion to hold items such as a headrest. A portion of the bib can be elongated to cover the midsection of the patient.

There has thus been outlined, rather broadly, the more important features of the invention in order that the detailed description thereof may be better understood, and in order that the present contribution to the art may be better appreciated. There are additional features of the invention that will be described hereinafter and which will form the subject matter of the claims appended hereto. The features listed herein and other features, aspects and advantages of the present invention will become better understood with reference to the following description and appended claims. The accompanying drawings, which are incorporated in and constitute part of this specification, illustrate embodiments of the invention and, together with the description, serve to explain the principles of the invention.

SUMMARY OF THE INVENTION

It is a principal object of the invention to provide a medical bib that protects the patient from unwanted substances and materials contacting his or her clothes or skin located beneath his or her face.

It is another object of the invention to provide a medical bib that also acts as a headrest cover to reduce the spread of disease between patients that use the same headrest over a period of time.

It is an additional object of the invention to provide a medical bib with an integrated hairnet such that the hairnet has a lower likelihood of accidentally becoming dislodged or removed from the patient.

It is yet another object of the invention to provide a medical bib that includes a cutout tissue portion conveniently located near the patient's face that can be used to absorb and removed unwanted substances without the use of an additional tissue or cloth.

It is a further object of this invention to provide a medical bib that is easy to use such that a patient can quickly and efficiently put on and remove the medical bib.

It is a final object of this invention to provide a device that is disposable so that no portion of the device that comes in direct contact with the patient or other unwanted matter is reused with another patient, thereby reducing the possibility of spreading diseases between patients.

It should be understood that while the preferred embodiments of the invention are described in some detail herein, the present disclosure is made by way of example only and that variations and changes thereto are possible without departing from the subject matter coming within the scope of the following claims, and a reasonable equivalency thereof, which claims I regard as my invention.

DETAILED DESCRIPTION OF THE FIGURES

Figure 1:
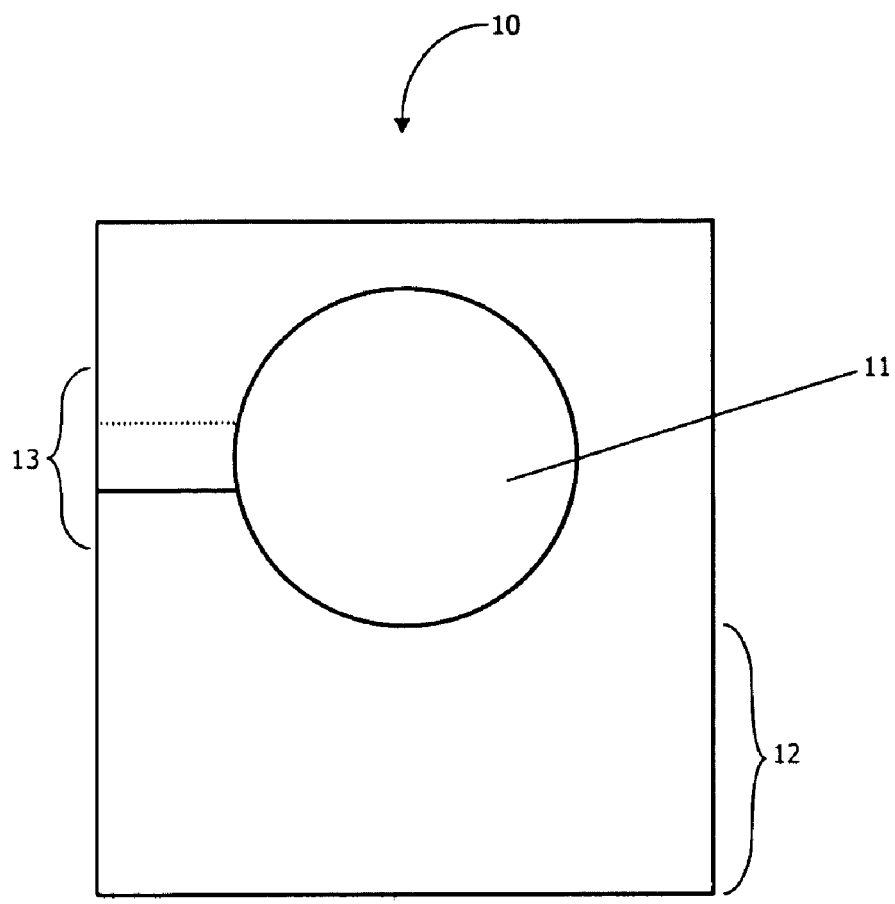
FIG. 1 is a front view of the medical bib.

Many aspects of the invention can be better understood with reference to the drawings below. The components in the drawings are not necessarily drawn to scale. Instead, emphasis is placed upon clearly illustrating the components of the present invention. Moreover, like reference numerals designate corresponding parts through the several views in the drawings.

FIG. 1 is a front view of the medical bib. A medical bib 10 includes a hole for the patient's neck 11. The hole for the patient's neck 11 should be large enough to fit any sized neck of a patient, yet small enough so that areas around the patient's neck are not unnecessarily exposed. While the inventor contemplates bibs with different sized and shaped holes, the inventor has found that a 10-inch diameter hole is appropriate for most uses. There is also a chest protection portion 12 that protects the chest area below the patient's face. A patient dons the medical bib 10 by placing the patient's neck through the hole for the patient's neck 11 and then securing the attachment portion 13 of the medical bib 10 such that the patient's neck is completely surround by the medical bib 10. The medical bib 10 itself can be made of various materials that are inexpensive to manufacture and use, including both absorbent and water repellant materials. An absorbent material can be used if a material that retains liquids is required. A water repellant material can be used if liquids are not desired to penetrate the medical bib 10. A combination of materials is also possible, where one side is absorbent and the other is water repellent. In this iteration, the absorbent can be used to retain liquids, while the water repellent side prevents the liquids from penetrating through the medical bib 10 and contacting the patient's clothes or skin below the medical bib 10.

Figure 2:
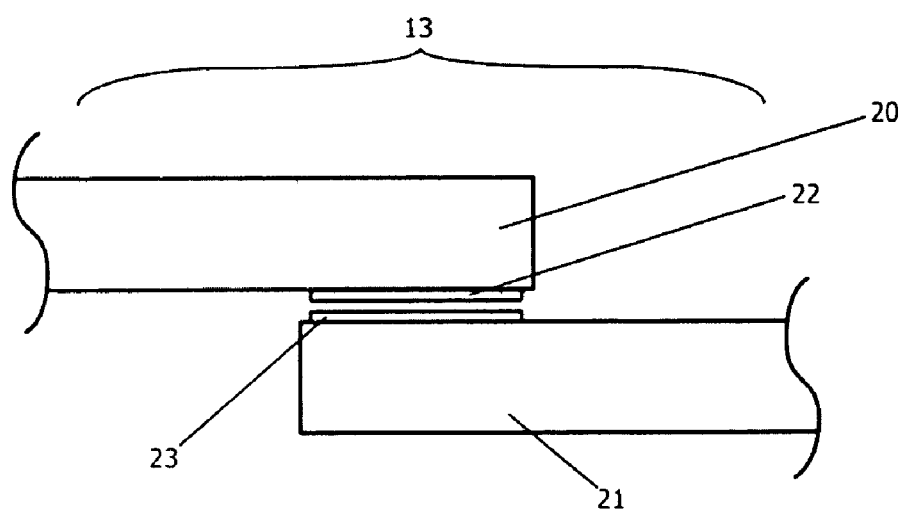
FIG. 2 is a blown up cut-away side view of the attachment portion of the medical bib.

FIG. 2 is a blown up cut-a-way side view of the attachment portion of the medical bib. The attachment portion 13 includes an upper attachment portion 20 and a lower attachment portion 21 that overlap each other. Attached to the upper attachment portion 20 is an upper means of attachment 22. Attached to the lower attachment portion 21 is a lower means of attachment 23. The upper means of attachment 22 and the lower means of attachment 23 can be secured together, thereby attaching the upper attachment portion 20 to the lower attachment portion 21. This result can be used to secure the medical bib around the patient's neck. There are different means to secure the upper means of attachment 22 to the lower means of attachment 23. One possible mean is by using magnets. The upper means of attachment 22 and the lower means of attachment 23 can each be a magnet, where each magnet is attracted to the other. Extremely weak magnets can be used because the amount of force required to keep the upper attachment portion 20 secured to the lower attachment portion 22 is small. It is envisioned by the inventor that small, thin sheets of magnetic material be used as the upper means of attachment 22 and the lower means of attachment 23, as they are small, lightweight, and inexpensive. An alternative means to attach the upper attachment portion 20 to the lower attachment portion 21 is by using static electricity. The upper means of attachment 22 and the lower means of attachment 23 can each be statically charged, but with opposite polarity. This small electrical force will cause the upper attachment portion 20 and the lower attachment portion 21 to stick together when placed in close proximity. An additional means of attaching the upper attachment portion 20 to the lower attachment portion 22 is by using snaps. The upper means of attachment 22 can be a male or female snap and the lower means of attachment 23 can be the opposite; if the upper means of attachment 22 is a male snap, then the lower means of attachment 23 would be a female snap. The opposite is also possible, where the upper means of attachment 22 is a female snap and the lower means of attachment 23 is a male snap. Various shapes and materials can be used for the snaps, so long as the snaps work together and can secure the upper attachment portion 20 to the lower attachment portion 21. Adhesive means can also be used as the means to secure the upper attachment portion 20 to the lower attachment portion 21. The upper means of attachment 22, the lower means of attachment 23, or both can be an adhesive. If both are an adhesive, then the upper means of attachment 22 and the lower means of attachment 23 stick to each other when placed together, thereby securing the medical bib around the patient's neck. If either one is an adhesive, then the opposing means of attachment can be nonexistent, as the adhesive will stick to the opposing attachment portion. Various strengths of adhesive can be used depending on its intended use. Weak adhesives can be used is it is desired that the medical bib be removed via separating the upper attachment portion 20 from the lower attachment portion 21. On the other hand, strong adhesives can be used to permanently secure the upper attachment portion 20 to the lower attachment portion 21, where the medical bib can be removed form the patient by ripping a portion of the medical bib. In this embodiment, it may be beneficial to have a protective sheet over each of the adhesives such that inadvertent contact between the upper attachment portion 20 and the lower attachment portion 21 does not cause the two sides to become secured together. A further means to attach the upper attachment portion 20 to the lower attachment portion 21 is by using hook and loop fasteners, otherwise known as Velcro®.

Figure 3:
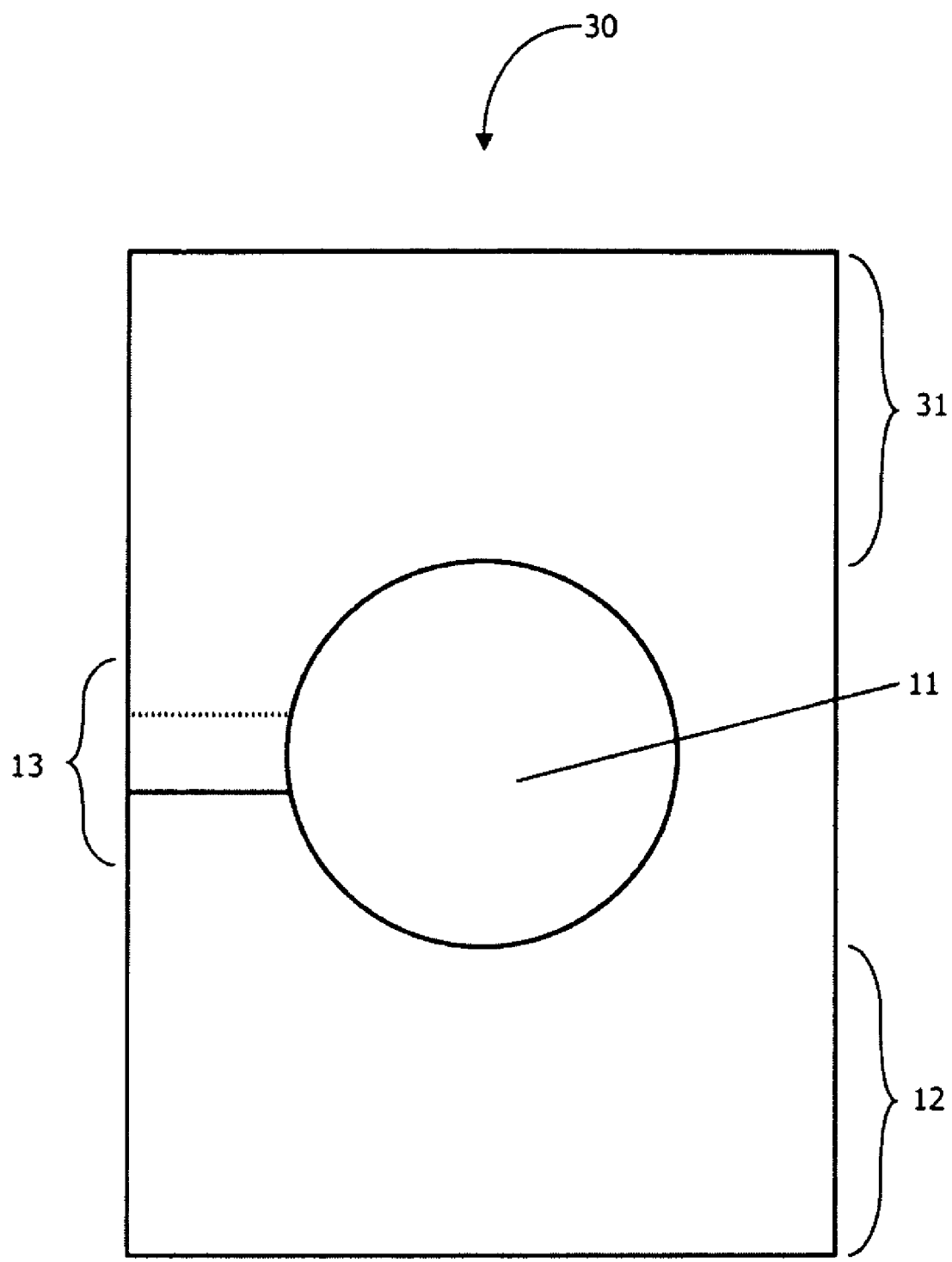
FIG. 3 is a front view of the medical bib with a headrest cover.

FIG. 3 is a front view of the medical bib with a headrest cover. A medical bib with headrest cover 30 includes a hole for the patient's neck 11. There is also a chest protection portion 12 that protects the chest area below the patient's face. On the opposite end from the chest protection portion 12 is a headrest cover portion 31, which keeps the patient's head from coming in direct contact with a headrest that supports the patient's head. A patient dons the medical bib with headrest cover 30 by placing the patient's neck through the hole for the patient's neck 11 and then securing the attachment portion 13 of the medical bib with headrest cover 30 such that the patient's neck is completely surrounded by the medical bib with headrest cover 30.

Figure 4:
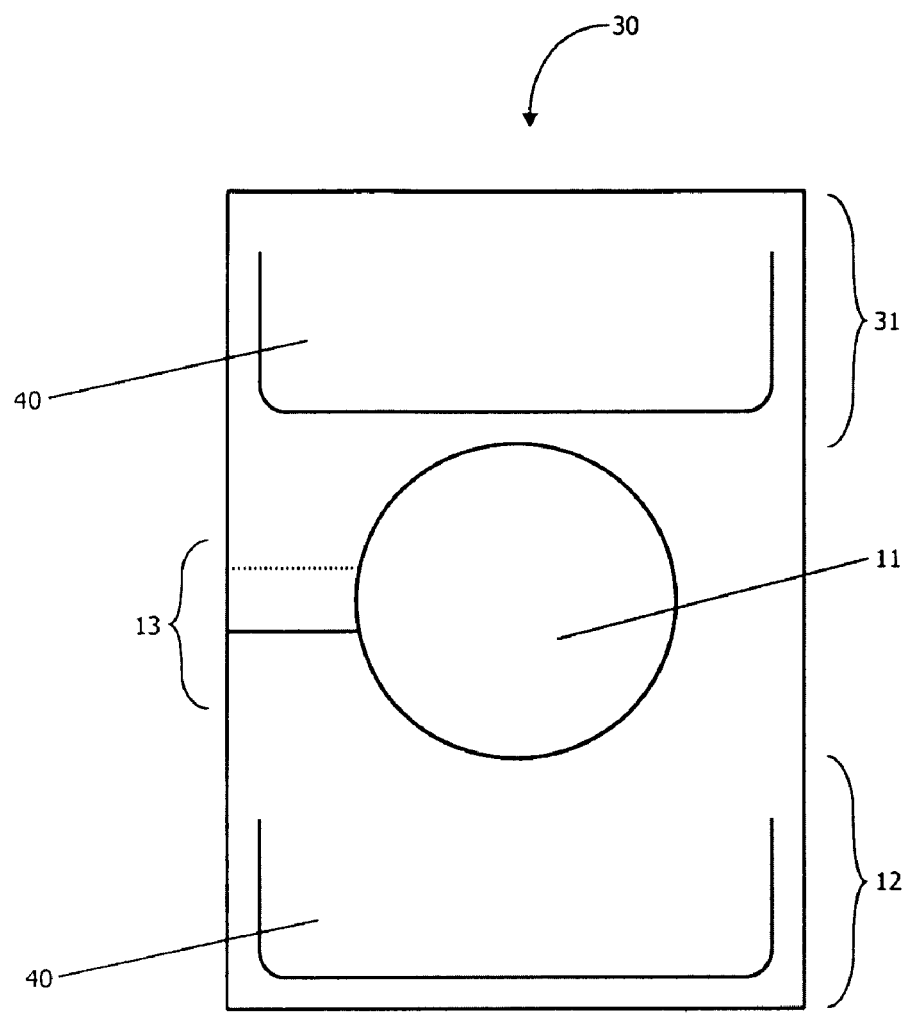
FIG. 4 is a front view of the medical bib with a headrest cover that includes pockets.

FIG. 4 is a front view of the medical bib with a headrest cover that includes pockets. A medical bib with headrest cover 30 includes a hole for the patient's neck 11. There is also a chest protection portion 12 that protects the chest area below the patient's face. On the opposite end from the chest protection portion 12 is a headrest cover portion 31, which keeps the patient's head from coming in direct contact with a headrest that supports the patient's head. A patient dons the medical bib with headrest cover 30 by placing the patient's neck through the hole for the patient's neck 11 and then securing the attachment portion 13 of the medical bib with headrest cover 30 such that the patient's neck is completely surround by the medical bib with headrest cover 30. In this embodiment, the chest protection portion 12 and the headrest cover portion 31 each include a pocket 40. The pockets 40 can be used for various purposes. The pocket 40 located in the chest protection portion 12 can be used to collect fluids or other substances that would normally slide down the medical bib and off onto the patient. The pocket 40 located in the headrest cover portion 31 can be used to house a disposable or reusable headrest. Different sized disposable headrests can be used to create a headrest of different heights and support, either to meet the comfort needs of the patient or the needs of the particular procedure that the patient is undergoing. A reusable headrest can be used with multiple patients since it is inserted into the pocket 40 located in the headrest cover portion 31. The patient using the medical bib with headrest cover 30 will not come in direct contact with the reusable headrest since it is located inside of the pocket 40, thereby providing the use of a headrest with a lower possibility of transmission of disease between patients. Means of closing and securing the disposable or reusable headrest within the pocket 40 are contemplated by the inventor, and include hook and loop fasteners, snaps, magnets, adhesives, and static electricity.

Figure 5:
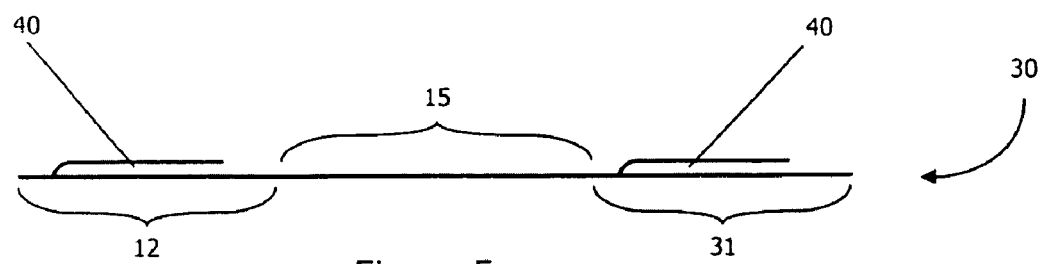
FIG. 5 is a cut-away side view of the medical bib with a headrest cover that also has pockets.

FIG. 5 is a cut-away side view of the medical bib with a headrest cover that also has pockets. The patient places his or her neck through a neck portion 15 of the medical bib with headrest cover 30. The chest protection portion 12 protects the chest area below the patient's face. On the opposite end from the chest protection portion 12 is a headrest cover portion 31, which keeps the patient's head from coming in direct contact with a headrest that supports the patient's head. In this embodiment, the chest protection portion 12 and the headrest cover portion 31 each include a pocket 40. The pockets 40 can be used for various purposes. The pocket 40 located in the chest protection portion 12 can be used to collect fluids or other substances that would normally slide down the medical bib and off onto the patient. The pocket 40 located in the headrest cover portion 31 can be used to house a disposable or reusable headrest. Different sized disposable headrests can be used to create a headrest of different heights and support, either to meet the comfort needs of the patient or the needs of the particular procedure that the patient is undergoing. A reusable headrest can be used with multiple patients since it is inserted into the pocket 40 located in the headrest cover portion 31. This reusable headrest can be used with multiple patients since it is inserted into the pocket 40 located in the headrest cover portion 31. The patient using the medical bib with headrest cover 30 will not come in direct contact with the reusable headrest since it is located inside of the pocket 40, thereby providing the use of a headrest with a lower possibility of transmission of disease between patients.

Figure 6:
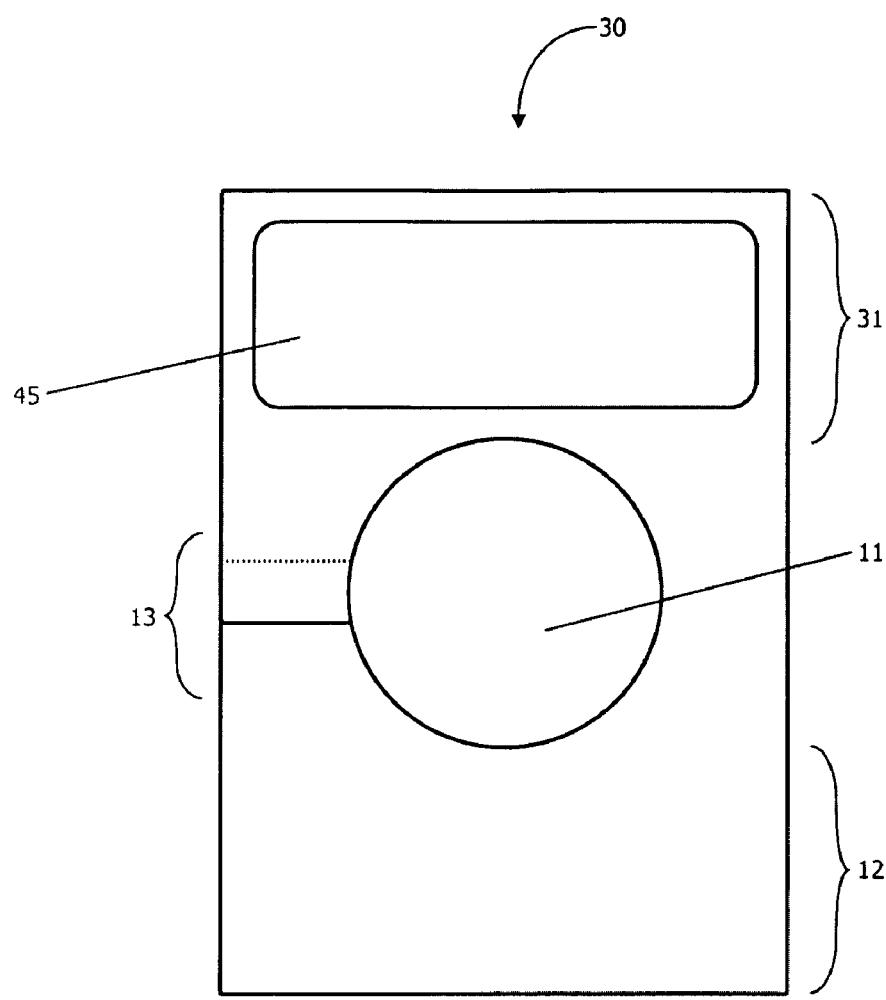
FIG. 6 is a front view of the medical bib with headrest cover that has a built in headrest.

FIG. 6 is a front view of the medical bib with headrest cover that has a built in headrest. A medical bib with headrest cover 30 includes a hole for the patient's neck 11. There is also a chest protection portion 12 that protects the chest area below the patient's face. On the opposite end from the chest protection portion 12 is a headrest cover portion 31, which keeps the patient's head from coming in direct contact with a headrest that supports the patient's head. A patient dons the medical bib with headrest cover 30 by placing the patient's neck through the hole for the patient's neck 11 and then securing the attachment portion 13 of the medical bib with headrest cover 30 such that the patient's neck is completely surround by the medical bib with headrest cover 30. In this embodiment of the medical bib with headrest cover 30, the headrest cover has a built in headrest 45. The headrest 45 should manufactured such that it provides comfortable support to the patient and at the same time is inexpensive to create, as the built in headrest 45 will be disposed of with the medical bib with headrest cover 30 after every use.

Figure 7:
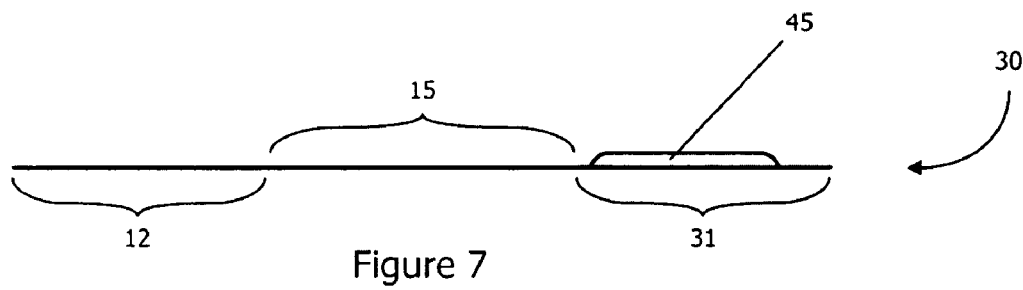
FIG. 7 is a cut-away side view of the medical bib with a headrest cover that has a built in headrest.

FIG. 7 is a cut-away side view of the medical bib with a headrest cover that has a built in headrest. The patient places his or her neck through the neck portion 15 of the medical bib with headrest cover 30. The chest protection portion 12 protects the chest area below the patient's face. On the opposite end from the chest protection portion 12 is a headrest cover portion 31, which keeps the patient's head from coming in direct contact with a headrest that supports the patient's head. In this embodiment, the headrest cover portion 31 each includes a built in headrest 45.

Figure 8:
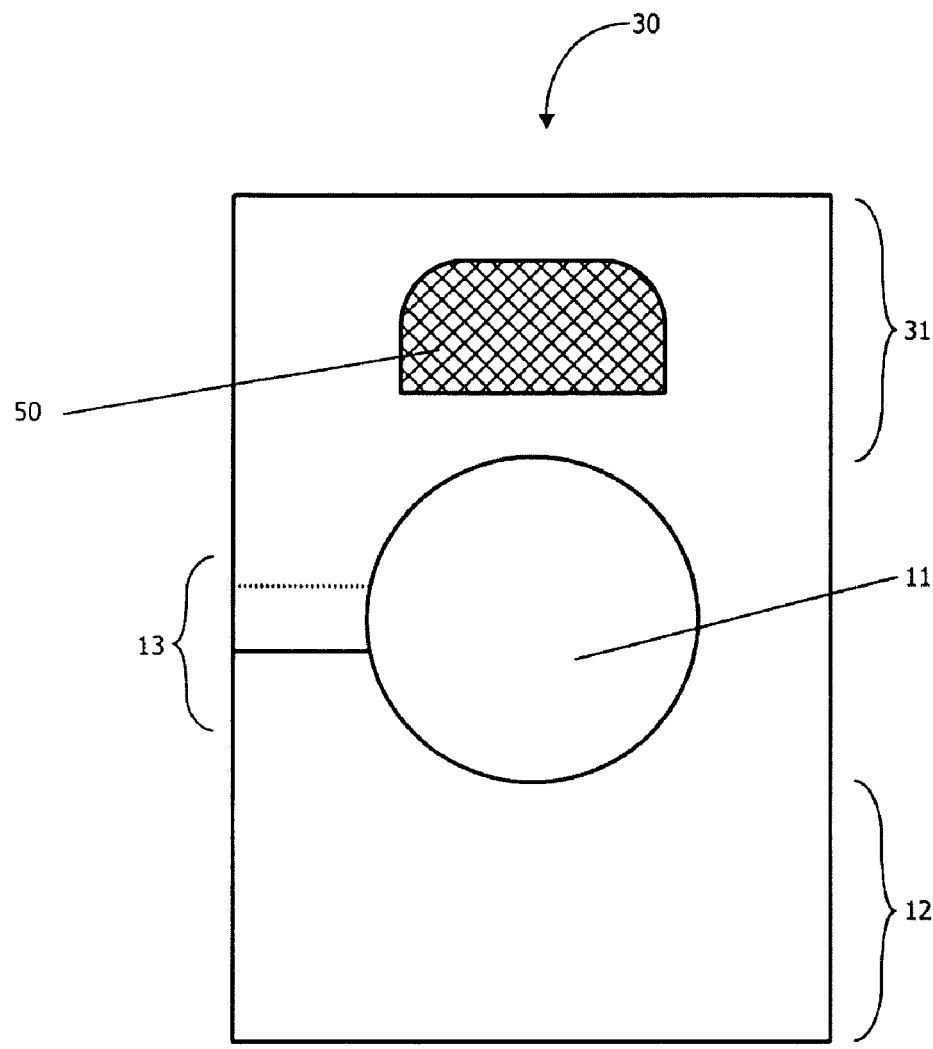
FIG. 8 is a front view of the medical bib with headrest cover that includes a hairnet.

FIG. 8 is a front view of the medical bib with headrest cover that includes a hairnet. A medical bib with headrest cover 30 includes a hole for the patient's neck 11. There is also a chest protection portion 12 that protects the chest area below the patient's face. On the opposite end from the chest protection portion 12 is a headrest cover portion 31, which keeps the patient's head from coming in direct contact with a headrest that supports the patient's head. A patient dons the medical bib with headrest cover 30 by placing the patient's neck through the hole for the patient's neck 11 and then securing the attachment portion 13 of the medical bib with headrest cover 30 such that the patient's neck is completely surround by the medical bib with headrest cover 30. In this embodiment of the medical bib with headrest cover 30, the headrest cover includes a hairnet 50. Hairnets are often used when the patient undergoes procedures where it is desirable to restrict the movement of the patient's hair. The hairnet 50 should include an elastic portion so that it can stretch around and fit securely to a patient's head after the patient has donned the medical bib with headrest cover 30. Because the hairnet 50 is connected to the medical bib with headrest cover 30, it has less of a chance of becoming dislodged or removed from the patient's head since the medical bib with headrest cover 30 is also secured to the patient.

Figure 9:
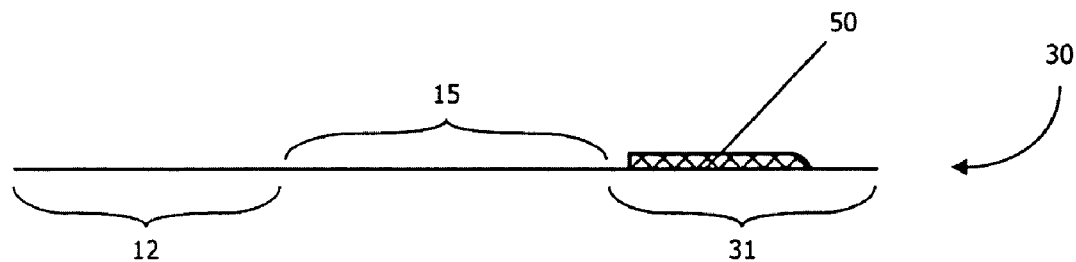
FIG. 9 is a cut-away side view of the medical bib with a headrest cover that includes a hairnet.

FIG. 9 is a cut-away side view of the medical bib with a headrest cover that includes a hairnet. The patient places his or her neck through the neck portion 15 of the medical bib with headrest cover 30. The chest protection portion 12 protects the chest area below the patient's face. On the opposite end from the chest protection portion 12 is a headrest cover portion 31, which keeps the patient's head from coming in direct contact with a headrest that supports the patient's head. In this embodiment, the headrest cover portion 31 each includes a hairnet 50.

Figure 10:
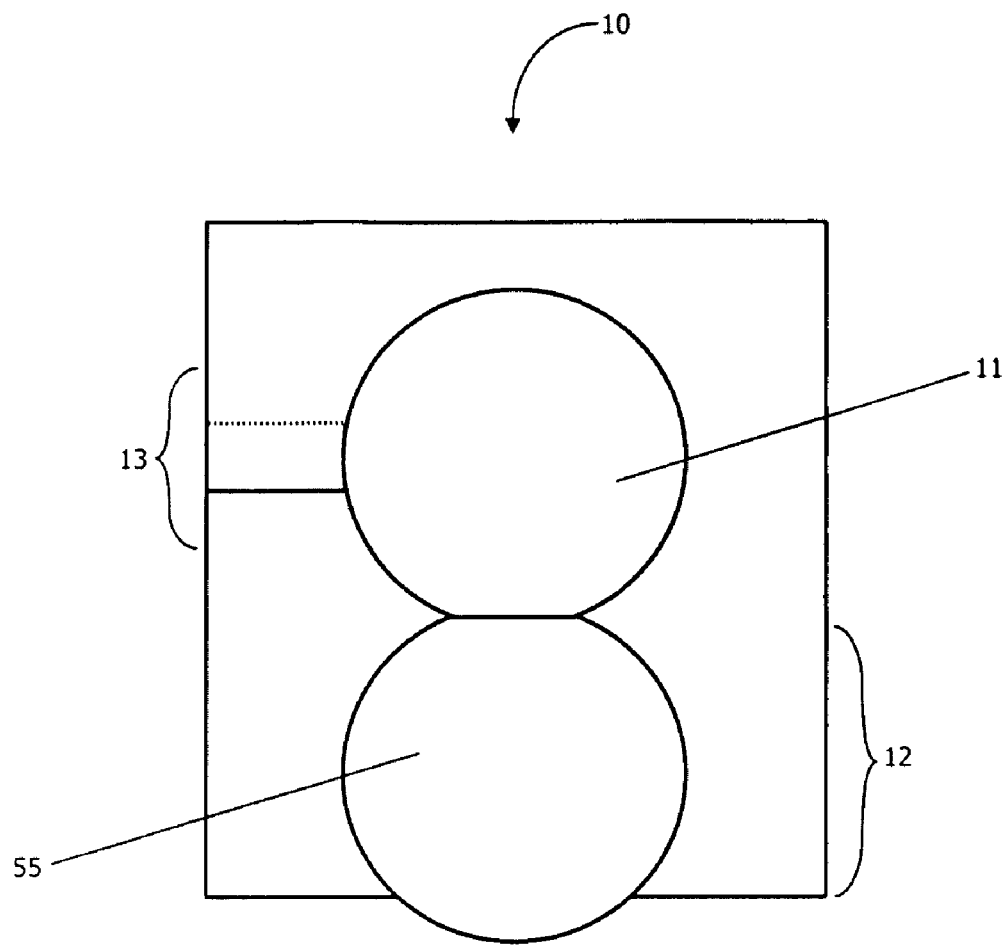
FIG. 10 is a front view of the medical bib with an integrated cutout tissue.

FIG. 10 is a front view of the medical bib with an integrated cutout tissue. In this embodiment of the medical bib 10, the hole for the patient's neck 11 contains a cutout tissue 55. This cutout tissue can be made from the same material as the rest of the medical bib 10 or of a different material, so long as the material is absorbent and can be used in the same fashion as a tissue or cloth. This cutout tissue 55 can be secured to the medical bib 10 my means of perforation, where the cutout tissue 55 can be torn and completely removed from the medical bib 10 to create the hole for the patient's neck 11. Alternatively, as shown in the figure, a portion of the cutout tissue 55 can remain secured to the medical bib 10 such that when partially removed from the medical bib 10, the cutout tissue 55 remains close to the patient's face. There is also a chest protection portion 12 that protects the chest area below the patient's face. A patient dons the medical bib 10 by placing the patient's neck through the hole for the patient's neck 11 and then securing the attachment portion 13 of the medical bib 10 such that the patient's neck is completely surround by the medical bib 10. The cutout tissue 55 can be used for various purposes, including as a tissue to absorb substances or as an instrument tray cover to use during the procedure.

Figure 11:
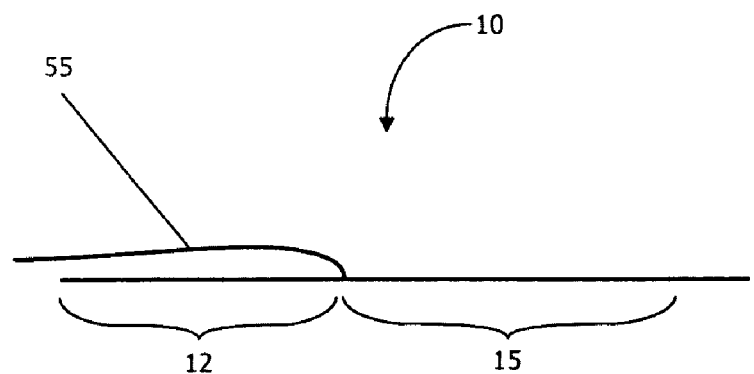
FIG. 11 is a cut-away side view of the medical bib with an integrated cutout tissue.

FIG. 11 is a cut-away side view of the medical bib with an integrated cutout tissue. The patient places his or her neck through the neck portion 15 of the medical bib 10. The chest protection portion 12 protects the chest area below the patient's face. In this embodiment, the cutout tissue 55 is partially removed from the medical bib 10 such that the cutout tissue 55 remains close to the patient's face.

While the hole for the patient's neck 11 is shown in the various figures as a circular cutout portion, it is contemplated by the inventor that this could be any shape, including square, rectangle, oval, polygon, or the like, so long as the patient's neck will fit through the hole. The hole for the patient's neck 11 could be empty, or could contain a material that is either the same as the rest of the bib or different. If the hole for the patient's neck 11 is not empty, then the material inside of the hole for the patient's neck 11 must be removed before donning the bib. This removed material can then be used for other purposes, such as a tissue, protective cover for an instrument tray, or the like.

It is also contemplated by the inventor that the chest protection portion 12 can extend beyond the chest area of the patient to include the lower torso region, or even to the legs and feet of the patient. If the chest protection portion 12 does extend beyond the chest area of the patient, such as when the patient is undergoing surgery, it is further contemplated that chest protection portion 12 include one or more straps (not shown). These straps can be used to secure wires, hoses, or the like in place while the bib is in use. These straps can be permanently secured to the bib on one end, and have a means of attachment on the other end, which could include hook and loop fasteners, magnets, adhesives, static electricity, or any other means of inexpensive attachment. The straps could be located in various locations about the bib with the purpose of securing wires hoses, or the likes, during the use of the bib. Preferably, a strap is about 2 inches in length from end to end, and is about 1 inch in width. It is located in the chest protection portion 12 approximately where the waist of the patient would be.

I claim:

1. A bib for use in medical or dental procedures comprising:
    a hole, a chest protection portion, a means of attachment, and a headrest cover portion,
    where the hole is of a sufficient size such that a patient's neck will fit inside of the hole, and where the hole is small enough that the areas around the patient's neck are not unnecessarily exposed,
    where the chest protection portion is located over the chest and below the face of the patient when the bib is worn by the patient, where the width of the chest protection portion is greater than the width of the hole, where the length of the chest protection portion is sufficient to protect the patient's chest area from unwanted liquids and other substances from contacting his or her clothes or skin,
    where the means of attachment secures the bib to the patient, where the means of attachment is located on one side of the bib, where the means of attachment secures the bib to the patient by securing together two overlapping layers of the bib,
    where the materials used to manufacture the bib comprise absorbent materials, water repellent materials, or both, and where the bib is designed and manufactured to be disposable so that the bib is not intended to be used on multiple different patients, and
    where the headrest cover portion is located behind the head of the patient when the bib is worn by the patient, where the width of the headrest cover portion is greater than the diameter of the hole, and where the length of the headrest cover portion is sufficient to prevent a patient's head from coming in direct contact with any support located beneath his or her head, where the headrest cover portion comprises a hairnet, where the hairnet comprises an elastic portion, where the elastic portion can stretch around the patient's head.

2. The bib of claim 1, where the means of attachment secures together the two overlapping layers of the bib through the use of magnets.

3. The bib of claim 1, where the means of attachment secures together the two overlapping layers of the bib through the use of snaps.

4. The bib of claim 1, where the means of attachment secures together the two overlapping layers of the bib through the use of hook and loop fasteners.

5. The bib of claim 1, where the means of attachment secures together the two overlapping layers of the bib through the use of static electricity.

6. The bib of claim 1, where the means of attachment secures together the two overlapping layers of the bib through the use of adhesives on either or both of the two overlapping layers of the bib.

7. The bib of claim 1, where the bib further comprises a cut-out tissue, where the cut-out tissue is located within the hole before use, and is partially or completely removed from the hole before the patient dons the bib, where the cut-out tissue comprises one or more materials capable of absorption.

8. The bib of claim 1, where the chest protection portion extends beyond the waist of the user.

9. A bib for use in medical or dental procedures comprising:
    a hole, a chest protection portion, a headrest cover portion, a means of attachment, and a cut-out tissue,
    where the hole is of a sufficient size such that a patient's neck will fit inside of the hole, and where the hole is small enough that the areas around the patient's neck are not unnecessarily exposed,
    where the chest protection portion is located over the chest and below the face of the patient when the bib is worn by the patient, where the width of the chest protection portion is greater than the width of the hole, where the length of the chest protection portion is sufficient to protect the patient's chest area from unwanted liquids and other substances from contacting his or her clothes or skin,
    where the headrest cover portion is located behind the head of the patient when the bib is worn by the patient, where the width of the headrest cover portion is greater than the width of the hole, and where the length of the headrest cover portion is sufficient to prevent a patient's head from coming in direct contact with any support located beneath his or her head, where the headrest cover portion comprises a hairnet, where the hairnet comprises an elastic portion, where the elastic portion can stretch around the patient's head,
    where the means of attachment secures the bib to the patient, where the means of attachment is located on one side of the bib, where the means of attachment secures the bib to the patient by securing together two overlapping layers of the bib, and where the materials used to manufacture the bib comprise absorbent materials, water repellent materials, or both, and where the bib is designed and manufactured to be disposable so that the bib is not intended to be used on multiple different patients, where the cut-out tissue is located within the hole before use, and is completely removed from the hole before the patient dons the bib, where the cut-out tissue comprises one or more materials capable of absorption.

10. The bib of claim 9, where the means of attachment securing together the two overlapping layers of the bib is selected from the group consisting of magnets, snaps, hook and loop fasteners, static electricity, and adhesives.

11. A bib for use in medical or dental procedures consisting of:

a hole, a chest protection portion, a headrest cover portion, and a means of attachment, where the hole is of a sufficient size such that a patient's neck will fit inside of the hole, and where the hole is small enough that the areas around the patient's neck are not unnecessarily exposed, where the chest protection portion is located over the chest and below the face of the patient when the bib is worn by the patient, where the width of the chest protection portion is greater than the width of the hole, where the length of the chest protection portion is sufficient to protect the patient's chest area from unwanted liquids and other substances from contacting his or her clothes or skin, where the headrest cover portion is located behind the head of the patient when the bib is worn by the patient, where the width of the headrest cover portion is greater than the width of the hole, and where the length of the headrest cover portion is sufficient to prevent a patient's head from coming in direct contact with any support located beneath his or her head, where the headrest cover portion comprises a hairnet, where the hairnet comprises an elastic portion, where the elastic portion can stretch around the patient's head, where the means of attachment secures the bib to the patient, where the means of attachment is located on one side of the bib, where the means of attachment secures the bib to the patient by securing together two overlapping layers of the bib, where the materials used to manufacture the bib comprise absorbent materials, water repellent materials, or both, and where the bib is designed and manufactured to be disposable so that the bib is not intended to be used on multiple different patients.

* * * * *